United States Patent [19]

Steele

[11] Patent Number: 5,322,440
[45] Date of Patent: Jun. 21, 1994

[54] DENTAL SYRINGE TIP

[75] Inventor: Charles E. Steele, Canton, Mich.

[73] Assignee: Kerr Manufacturing Company, Romulus, Mich.

[21] Appl. No.: 964,007

[22] Filed: Oct. 20, 1992

[51] Int. Cl.⁵ .................... A61C 5/04; A61M 5/315
[52] U.S. Cl. ........................................ 433/90; 604/218
[58] Field of Search ............................ 433/80, 89, 90; 604/218, 219, 221, 222, 225, 230, 311; 222/386, 326

[56] References Cited

U.S. PATENT DOCUMENTS

| D. 287,053 | 12/1986 | Bucchianeri et al. . | |
|---|---|---|---|
| D. 315,956 | 4/1991 | Dragan . | |
| 458,253 | 8/1891 | Reichardt | 604/219 |
| 3,320,954 | 5/1967 | Cowley . | |
| 3,581,956 | 6/1971 | Reid | 222/386 |
| 3,760,503 | 9/1973 | Baskas . | |
| 4,000,741 | 1/1977 | Binard et al. . | |
| 4,330,280 | 5/1982 | Dougherty et al. . | |
| 4,391,590 | 7/1983 | Dougherty . | |
| 4,472,141 | 9/1984 | Dragan . | |
| 4,482,950 | 7/1987 | Dragan . | |
| 4,492,576 | 1/1985 | Dragan . | |
| 4,636,202 | 1/1987 | Lowin et al. | 604/218 X |
| 4,758,158 | 6/1988 | Pierce et al. | 433/90 |
| 4,784,607 | 11/1988 | Francois . | |
| 4,820,278 | 4/1989 | Balisky | 604/230 X |
| 4,963,093 | 10/1990 | Dragan . | |
| 4,969,816 | 11/1990 | Drumm . | |
| 4,993,948 | 2/1991 | Cameron et al. . | |
| 5,004,124 | 4/1991 | Stefaniak et al. . | |
| 5,052,927 | 10/1991 | Discko, Jr. . | |
| 5,083,921 | 1/1992 | Dragan . | |
| 5,122,057 | 6/1992 | Discko, Jr. . | |
| 5,129,825 | 7/1992 | Discko, Jr. . | |

FOREIGN PATENT DOCUMENTS

| 45896 | 1/1899 | Fed. Rep. of Germany | 604/218 |
|---|---|---|---|
| 349449 | 5/1905 | France | 604/218 |
| 2291702 | 6/1976 | France | 604/218 |
| 1260103 | 1/1972 | United Kingdom | 604/218 |

Primary Examiner—Gene Mancene
Assistant Examiner—Nicholas D. Lucchesi
Attorney, Agent, or Firm—Wood, Herron & Evans

[57] ABSTRACT

A dental syringe tip having positioned in a material-containing passage therein a plug with a stepped nose configuration to minimize the force required to dispense material from the syringe tip. The stepped nose configuration also increases the amount of material dispensed from the syringe thereby reducing waste. The plug includes a sealing member to provide improved sealing between the plug and the internal surfaces defining the passage within the syringe tip.

10 Claims, 1 Drawing Sheet

DENTAL SYRINGE TIP

BACKGROUND OF THE INVENTION

1. Field of the Invention

This invention relates to a dental syringe tip, and more particularly to a dental syringe tip requiring less operator force to dispense the material therefrom.

2. Description of the Related Art

Dental syringe tips are typically purchased as capsules filled with a desired dental material such as an amalgam, etc. The syringe tip is inserted into a dental syringe; and upon the syringe being activated by an operator, a syringe plunger pushes a plug through an internal passage in the syringe tip thereby dispensing the dental material therefrom.

Since a dental syringe tip is held and operated in a hand held dental delivery gun by a dentist, it is desirable to minimize the forces required to dispense the material from the syringe tip, thereby improving control of the dental therapy. This feature is more important as formulated dental materials become more viscous. Further, it is desirable that the maximum amount of dental material pre-packaged in the syringe tip be dispensed, thereby minimizing material waste.

Known dental syringe tip designs may utilize a flat surface on the front, or forward, end of the plug contacting the dental material. That plug design provides an efficient longitudinal transfer of force from the operator to the dental material. However, since most dental syringe tips discharge the dental material through a tapered or narrow nozzle, a plug with a flat front end leaves undispensed dental material in the nozzle and other noncylindrical sections of the syringe tip located forwardly of the plug, thereby wasting that material.

To overcome that disadvantage, the front end of the plug may be formed into a conical, hemispherical or other shape that matches the interior geometry of the forward end of the syringe tip. Those shapes generally have rearwardly outwardly extending surfaces oblique to the longitudinal axis of the plug. Such plug designs will dispense more dental material than a plug with a flat front end. However, the oblique surfaces squeeze dental material between those surfaces and the mating surface inside the syringe tip thereby creating a greater reactive, or resistance, forces in a nonlongitudinal directions. Those nonlongitudinal forces increase the force required to push the dental material longitudinally through the syringe tip, thereby increasing the operator force required to dispense the material.

SUMMARY OF THE INVENTION

To overcome the disadvantages of existing dental syringe tips, a primary object of the present invention is to provide a dental syringe tip requiring less force to discharge the material than is possible with prior plug designs having conical, hemispherical or other complementary configurations.

According to the principles of the present invention, a dental syringe tip has a plug with a stepped-diameter nose configuration that minimizes the creation of nonlongitudinal resistance forces by the dental material, thereby reducing the force required to be applied by the operator.

The stepped-diameter nose configuration is formed by at least three coaxial cylindrical surfaces of successively greater diameters and longitudinally spaced from the front end of the plug. The first cylindrical surface has a circular end surface located at the forwardmost end of the plug and is perpendicular to a longitudinal axis of the plug. The other cylindrical surfaces have annular surfaces at their forward ends perpendicular to the longitudinal axis and intersecting adjacent cylindrical surfaces.

Pushing the dental material through the syringe tip with the stepped-diameter configuration formed by the cylindrical, circular and annular surfaces at the front end of the plug requires only longitudinal forces. By "longitudinal" force is meant a force in a direction parallel the desired direction of movement of the plug which is along the longitudinal axis of the syringe tip. Further, the stepped-diameter configuration of the plug extends into the nozzle of the syringe tip to dispense material therefrom without creating substantial nonlongitudinal forces which increase the force required by the operator. The plug further has a sealing member which utilizes the material being pushed to create a small radial force to provide a tight seal between the plug and the inside walls of the syringe tip.

DETAILED DESCRIPTION

Figure 1:
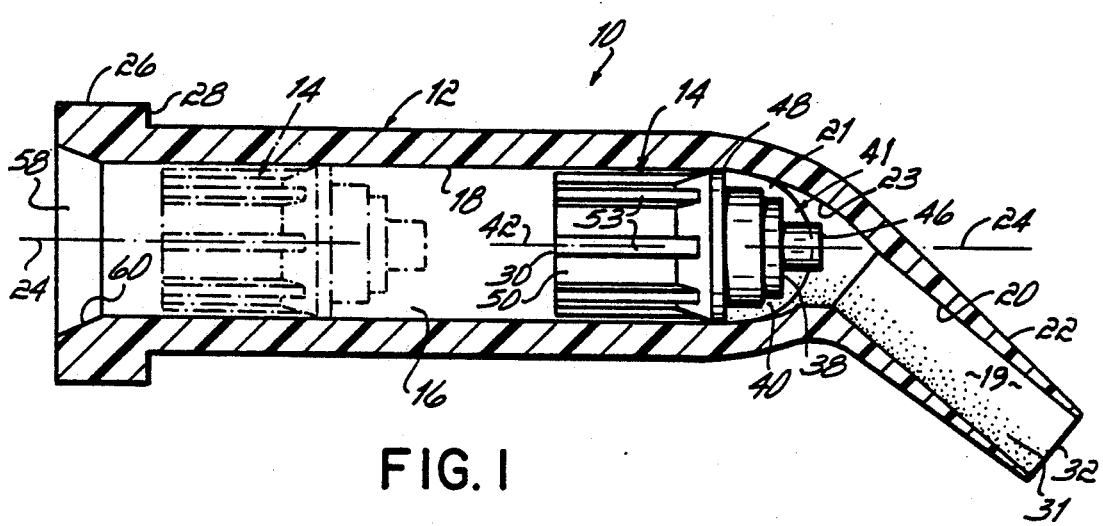
FIG. 1 is a cross-sectional view bisecting the syringe tip and illustrating the plug at two locations within the syringe tip.
Figure 2:
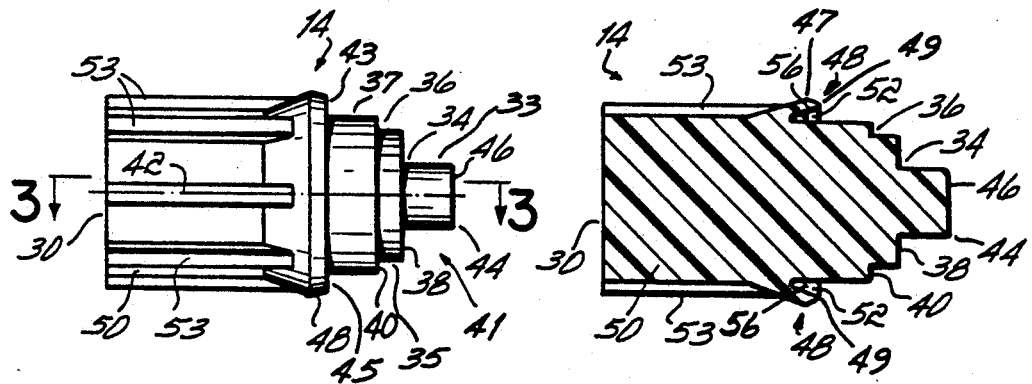
FIG. 2 is a side elevation of a plug.
Figure 3:
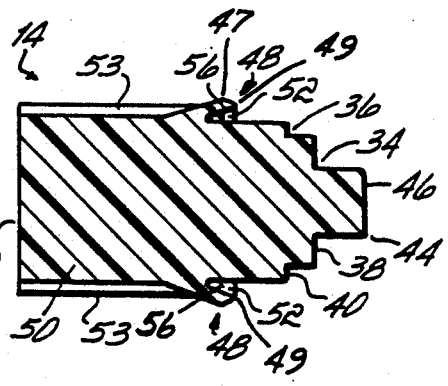
FIG. 3 is a cross-sectional view taken along lines 3—3 of FIG. 2.
Figure 4:
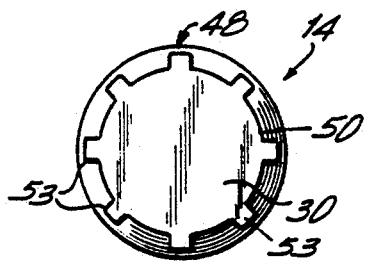
FIG. 4 is a rear-end view of the plug.
Figure 5:
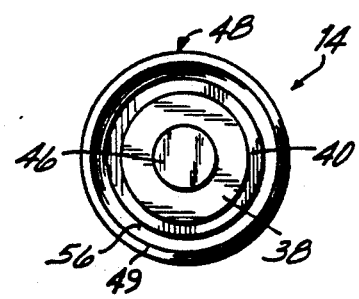
FIG. 5 is a front-end view of the plug.

The construction of the dental syringe tip of the present invention will be described with regard to FIGS. 1 through 5. A dental syringe tip 10 is comprised of a tube 12 and a plug 14. The tube 12 has an internal passage 16 bounded by a first internal cylindrical surface 18, a second smaller internal cylindrical surface 20 and a transitional surface 23 between said first and second internal surfaces 18 and 20, respectively. The tube 12 includes a nozzle 22 which intersects the tube 12 at an angle of approximately 40° with respect to a longitudinal axis 24 of the dental syringe tip 10. The internal passage within the nozzle 22 includes a volume 19 within the second internal surface 20 and a transitional volume 21 bounded by the transitional surface 23. The nozzle is configured and offset to provide a dentist with a line-of-sight over the syringe tip to the tooth on which work is being performed, thereby facilitating application of dental material to the tooth structure. The tube is preferably manufactured from Zytel 101 Nylon commercially available from Dupont.

One end of the tube 12 contains an annular flange 26 having an annular shoulder 28 which is used to secure the syringe tip 10 into a dental delivery gun(not shown). The use and operation of a dental syringe tip with a dental delivery gun is well known, and the dental syringe tip of the present invention may be used with a dental delivery gun commercially available from Centrix.

The plug 14 has a rear end 30 which contacts a plunger of a dental delivery gun (not shown) and transfers a longitudinal plunger force to dental material 31 within the interior of the tube 12 thereby dispensing the dental material from an outlet 32 at the forward end of the second internal surface 20. The plug has a nose at a front end 44 having a stepped-diameter configuration in contact with the material. The stepped-diameter configuration is formed by first, second and third cylindrical surfaces 33, 35 and 37, respectively, coaxial with the longitudinal axis 42 of the plug 14. The successive cylindrical surfaces 33, 35 and 37 are spaced rearwardly and longitudinally from the front end of the plug and are of successively greater diameters.

Cylindrical surface 33 having the smallest diameter has, at the forward-most end of the plug 14, a circular end surface 46 perpendicular to the longitudinal axis 42. Cylindrical surface 35 has, at its forward end, an annular end surface 38 perpendicular to the longitudinal axis 42 and intersecting the rearward end cylindrical surface 33. Cylindrical surface 37 having the largest diameter has, at its forward end, an annular surface 40 perpendicular to the longitudinal axis 42 and intersecting the rearward end of cylindrical surface 35. Cylindrical surface 33 and annular surface 38 form a first annular step 34, and cylindrical surface 35 and annular surface 40 form a second annular step 36.

The plug 14 also has a peripheral resilient sealing lip 48 which is forwardly outwardly directed from the main cylindrical body 50 of the plug 14 and is in contact with the first internal surface 18. A forwardly outwardly directed annular surface 56 on the sealing lip 48 forms an annular groove 52 with the body 50 of the plug 14. The sealing lip 48 has a diameter larger than the diameter of the third cylindrical surface 37. Further, the diameter of the sealing lip 48 is approximately 0.001 inches larger than the diameter of the first internal surface 18, and therefore, the sealing lip has an interference fit with the first internal surface 18.

As the plug 14 is pushed along the first internal surface 18 of the tube 12, material collects in the annular groove 52. The annular surface 56 of the sealing lip 48 is effective to create a small radially outwardly directed force component substantially perpendicular to the longitudinal axis 42 which forces the cylindrical wiping surface 47 of the sealing lip 48 against the first internal surface 18, thereby forming a tight seal with the first internal surface 18 and wiping the dental material therefrom. When forward motion of the plug fills the groove 52 with dental material, the annular surface 56 is also effective to present a horizontal force component at 43 over an annular area perpendicular to the longitudinal axis and bounded by the edge 49 of the lip 48 and the cylindrical surface 37. The annular area 43 and cylindrical surface 37 form a third annular step 45. The stepped-diameter configuration of the plug 14 is located forward of the sealing lip 48, the front edge 49 of which forms the rearward boundary of the stepped-diameter configuration 41.

A plurality of ribs 53 extend radially from the main cylindrical body 50 toward the first internal surface 18 and extend rearwardly from the sealing lip 48 to the rear end 30 of the plug 14. The function of the plurality of ribs 53 is to maintain the longitudinal axis 42 of the plug 14 substantially coaxial with the longitudinal axis 24 of the tube 12. Maintaining the plug 14 in coaxial alignment with the syringe tube 12 minimizes the creation of nonlongitudinal forces and helps minimize the force required by the operator. The diametric measurement across the ribs is approximately 0.002 inches less than the diameter of the first internal surface 18. In the event the plug loses alignment, the ribs minimize the area of contact of the plug 14 with the first internal surface 18 which helps to minimize the force required by the operator to move the plug 14 through the syringe tip 14.

The tube 12 has a rear opening 58 with an annular tapered wall 60 which facilitates compression of the sealing member 48 as the plug 14 is inserted into the tube 12. The plug 14 is constructed of a polypropylene material, part number P4G4Z001, commercially available from Eastman.

The circular surface 46, cylindrical surfaces 33, 35 and 37, annular surfaces 38 and 40 and annular area 43 combine to form steps 34, 36 and 43 of a stepped-diameter configuration 41 on the front end 44 of plug 14. The forward translation of the stepped nose configuration 41 pushes material solely longitudinally along axis 42 in the absence of nonlongitudinal forces, thereby minimizing the force required by the operator to push the plug 14 through the first internal surface 18. The rearwardly outwardly directed surfaces oblique to the longitudinal axis which are used at the front of other plug nose configurations create greater nonlongitudinal forces which require the application of a greater force by the operator to translate the plug. The stepped-diameter configuration 41 of the present invention which is located forward of the sealing member 48 extends into the transitional volume 21 of the nozzle 22 to dispense material therefrom.

While the invention has been illustrated in some detail according to the preferred embodiments shown in the accompanying drawings and while the preferred embodiments have been described in some detail, there is no intention to thus limit the invention to such detail. On the contrary, it is intended to cover all modifications, alterations and equivalents falling within the spirit and scope of the appended claims.

What is claimed is:

1. A dental syringe tip for dispensing material by applying a forwardly directed force substantially parallel to a longitudinal axis of the syringe tip, comprising:
    an internal passage having a longitudinal axis defining the longitudinal axis of the syringe tip and containing the material to be dispensed; and
    a plug located within said internal passage, said plug having
        a rear end responsive to the force,
        a front end in contact with the material, said front end of said plug having a stepped-diameter configuration substantially free of rearwardly outwardly directed oblique surfaces, said stepped-diameter configuration of said front end including at least two cylindrical surfaces of successively greater diameters longitudinally spaced from a forward-most point of said front end of said plug, and said cylindrical surfaces being joined by an annular surface substantially perpendicular to said longitudinal axis thereby forming an annular step,
        a peripheral sealing member rearward of said stepped diameter configuration and in contact with a surface bounding said internal passage, and
        a plurality of ribs extending longitudinally rearward of said peripheral sealing member toward said rear end of said plug.

2. The dental syringe tip of claim 1 wherein said plug has a longitudinal axis and said stepped-diameter configuration of said front end of said plug further comprises:
    a first cylindrical surface centrally located about the longitudinal axis of said plug and having a circular end surface located at a forward-most point of said front end of said plug;

a second cylindrical surface rearwardly displaced along the longitudinal axis of said plug from said first cylindrical surface; a diameter larger than a diameter of said first cylindrical surface;

a first annular surface approximately perpendicular to the longitudinal axis of said plug and intersecting a rearward end of said first cylindrical surface and a forward end of said second cylindrical surface;

a third cylindrical surface rearwardly displaced along the longitudinal axis of said plug from said second cylindrical surface and having a diameter larger than the diameter of said second cylindrical surface; and a second annular surface approximately perpendicular to the longitudinal axis of said plug and intersecting a rearward end of said second cylindrical surface and a forward end of said third cylindrical surface.

3. The dental syringe tip of claim 1 wherein said internal passage is cylindrical and said peripheral sealing member has a diameter larger than a diameter of said internal passage, said peripheral sealing member forming an annular groove between a forwardly outwardly directed annular surface of said peripheral sealing member and said plug, whereby a small radial force component is applied to said peripheral sealing member in response to material collecting in said groove during motion of said plug through said internal passage.

4. The dental syringe tip of claim 3 wherein said peripheral sealing member further comprises a cylindrical wiping surface in contact with a surface bounding said internal passage.

5. The dental syringe tip of claim 3 wherein said stepped-diameter configuration further includes an annular area formed between an edge of said sealing member and said third cylindrical surface.

6. The dental syringe tip of claim 1 wherein said plurality of ribs extend in a radial direction toward said surface bounding said internal passage and further extend longitudinally from said peripheral sealing member to said rear end of said plug.

7. A syringe tip for dispensing material, comprising:
an internal passage containing the material to be dispensed; and
a plug having a longitudinal axis and located in said internal passage, said plug having
a circular surface at a forward-most end in contact with the material and substantially perpendicular to the longitudinal axis of said plug,
at least three successive cylindrical surfaces coaxial with the longitudinal axis of said plug and successively displaced from said circular surface, said three successive cylindrical surfaces having successively greater diameters, and
at least two annular surfaces substantially perpendicular to the longitudinal axis of said plug, each of said annular surfaces extending between and intersecting two of said cylindrical surfaces.

8. A dental syringe tip for dispensing material comprising:
a tube containing material to be dispensed having an internal passage between a rear end of the dental syringe tip and an orifice dispensing the material at a forward end of the dental syringe tip; and a plug slidably located in said internal passage with a forward-most end in contact with the material, said plug having
a centrally located circular surface at said forward-most end approximately perpendicular to a longitudinal axis of said plug,
at least two annular surfaces substantially perpendicular to the longitudinal axis of said plug, said annular surfaces being successively rearwardly displaced from said circular surface and having successively larger diameters,
a peripheral resilient sealing lip in contact with a surface bounding said internal passage, and
a plurality of ribs extending in a radial direction toward said surface bounding said internal passage and extending longitudinally from a point rearward of the peripheral resilient sealing lip to a rearward-most end of said plug 9. A dental syringe tip for dispensing material comprising:
a tube containing the material to be dispensed and having a longitudinal axis, said tube further having an internal passage between a rear end of the dental syringe tip and an orifice dispensing material at a forward end of the dental syringe tip; and
a plug located in said internal passage and having a longitudinal axis therethrough, said plug further having
a cylindrical body with a forward-most end in contact with the material and a rear end,
a peripheral sealing lip located intermediate said forward-most and rear ends of said plug, said peripheral sealing lip being forwardly outwardly directed from said plug and contacting said internal passage rearward of the forward-most end of said plug, and
a plurality of ribs extending in a radial direction from said cylindrical body toward a surface bounding said internal passage, and said plurality of ribs extending longitudinally from said sealing lip to said rear end of said plug, said plurality of ribs maintaining said longitudinal axis of said plug coaxial with said longitudinal axis of said tube, thereby guiding said plug within said internal passage of said tube.

10. A plug for a dental syringe tip comprising:
a cylindrical body with a central longitudinal axis,
a front end having a stepped diameter configuration and including.
a first cylindrical surface centrally located about the longitudinal axis of said plug and having a circular end surface located at a forward-most point said front end of said plug;
a second cylindrical surface rearwardly displaced along the longitudinal axis of said plug from said first cylindrical surface and having a diameter larger than a diameter of said first cylindrical surface;
a first annular surface approximately perpendicular to the longitudinal axis of said plug and intersecting a rearward end of said first cylindrical surface and a forward end of said second cylindrical surface;
a third cylindrical surface rearwardly displaced along the longitudinal axis of said plug from said second cylindrical surface and having a diameter larger than the diameter of said second cylindrical surface;

a second annular surface approximately perpendicular to the longitudinal axis of said plug and intersecting a rearward end of said second cylindrical surface and a forward end of said third cylindrical surface;

a sealing member extending from said cylindrical body rearward of said third cylindrical surface; and a plurality of ribs extending radially from said cylindrical body and extending longitudinally from said sealing member toward a rear end of said plug.

* * * * *